United States Patent [19]

Chernosky et al.

[11] Patent Number: 5,097,963
[45] Date of Patent: Mar. 24, 1992

[54] STERILE PROTECTIVE SYSTEM FOR SURGICAL INSTRUMENTS DURING A SURGICAL OPERATION

[75] Inventors: Marvin E. Chernosky; Jay M. Chernosky, both of Houston, Tex.

[73] Assignee: Preven-A-Stik, Inc., Houston, Tex.

[21] Appl. No.: 508,980

[22] Filed: Apr. 12, 1990

[51] Int. Cl.[5] ................................................ A47F 7/00
[52] U.S. Cl. ................................. 211/60.1; 206/366
[58] Field of Search ............. 206/564, 363, 364, 365, 206/366, 367, 370, 571; 211/60.1, 70.6

[56] References Cited

U.S. PATENT DOCUMENTS

| D. 200,815 | 4/1965 | Chard | D58/13 |
|---|---|---|---|
| D. 293,469 | 12/1987 | Greenblatt | D24/25 |
| 1,647,154 | 11/1927 | Soybel . | |
| 1,812,781 | 6/1931 | Gibbs . | |
| 2,018,651 | 10/1935 | Bates | 206/370 |
| 2,099,906 | 11/1937 | Reese et al. | 132/79 |
| 2,639,081 | 5/1953 | Metzger | 229/42 |
| 2,659,485 | 11/1953 | Duley et al. | 206/72 |
| 2,664,005 | 12/1953 | Kosinski | 65/65 |
| 2,807,361 | 9/1957 | Junkin | 206/75 |
| 2,856,067 | 10/1958 | Sparks | 206/43 |
| 2,903,129 | 9/1959 | Anderson | 206/72 |
| 4,342,391 | 8/1982 | Schainholz | 206/370 |
| 4,344,532 | 8/1982 | Eldridge et al. | 206/363 X |
| 4,383,615 | 5/1983 | Aquino | 206/366 X |

Primary Examiner—Robert W. Gibson, Jr.
Attorney, Agent, or Firm—Arnold, White & Durkee

[57] ABSTRACT

A protective rack for temporarily storing surgical instruments during surgery includes a series of inclined grooves separated by partitions. The rack is disposable, and may be affixed to a surgical drape by coating the bottom flange with adhesive. Each groove supports the sharp end of a surgical instrument, and the inner surfaces of the grooves and partitions are formed of a flexible, resilient material.

22 Claims, 2 Drawing Sheets

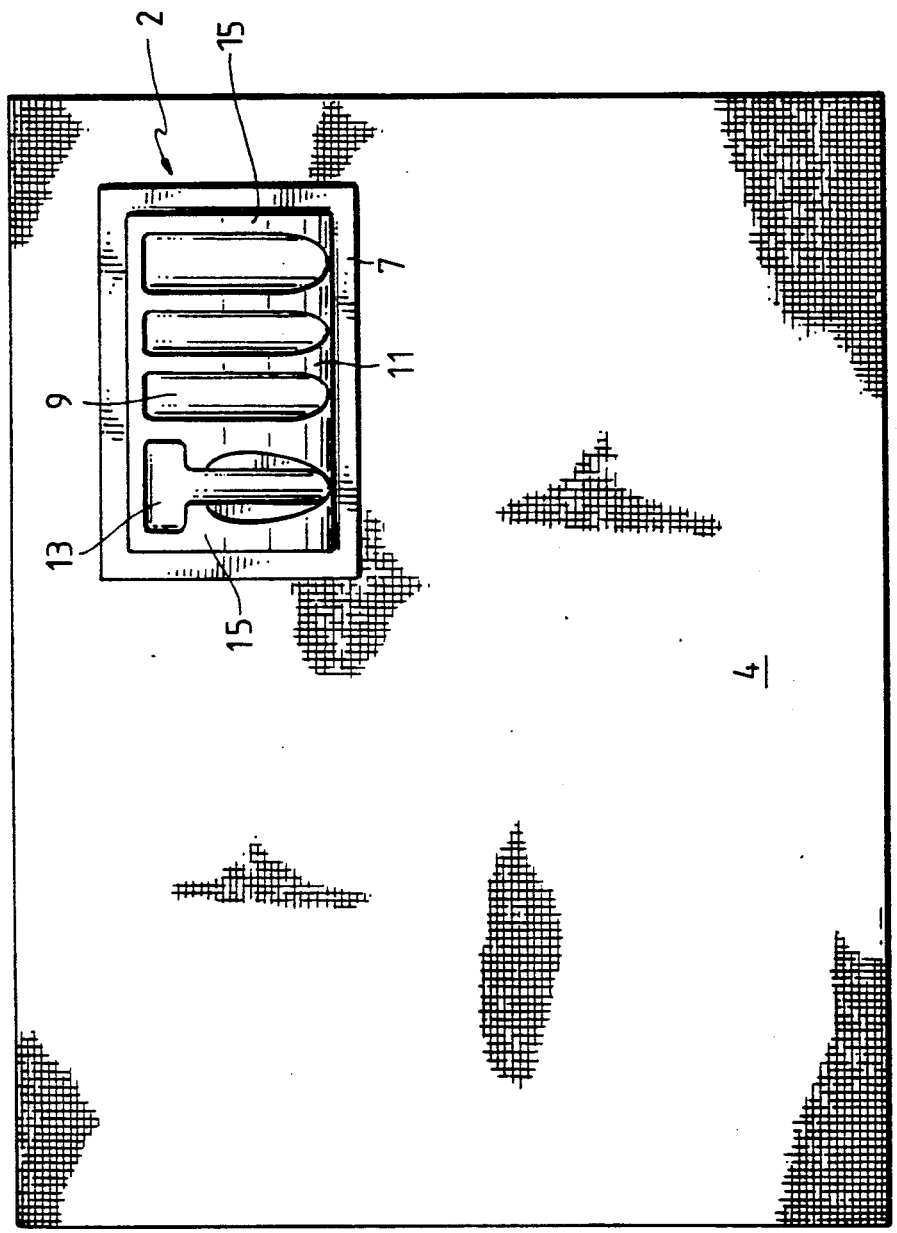

STERILE PROTECTIVE SYSTEM FOR SURGICAL INSTRUMENTS DURING A SURGICAL OPERATION

FIELD OF THE INVENTION

The present invention relates to a protective rack for surgical instruments. More specifically, the present invention relates to a sterile protective system for surgical instruments which reduces the danger of inadvertent puncture or laceration from such instruments during a surgical procedure.

DESCRIPTION OF THE PRIOR ART

Surgeons and other medical personnel involved in surgical procedures have long been concerned about contamination resultant from contact with blood or other bodily fluids of patients. These fluids all often carry infectious fluid-borne diseases such as hepatitis or the HIV AIDS virus. The danger of contamination is further compounded by the risk of contamination from inadvertent punctures or lacerations caused by hypodermic needles, scalpels or other medical instruments having sharpened edges or points.

To avoid problems associated with inadvertent punctures by hypodermic needles, many physicians have resorted to capping the needles after each use. Such precautionary procedures, however, are time consuming and themselves present a hazard of inadvertent puncture. Accordingly, recapping is generally not recommended by the medical community.

To avoid accidental laceration by sharpened scalpels or the like, such instruments are generally be organized on a surgical tray in a manner so as to reduce the possibility of contamination during instrument retrieval. Organization and grouping of medical instruments, however, are not always possible when surgeons perform unassisted operations as is often the case in outpatient surgery.

SUMMARY OF THE INVENTION

The present invention addresses the above and other disadvantages by providing a disposable, sterile protective system which is adapted to isolate the sharpened points or edges of surgical instruments. The system helps to prevent inadvertent contact by surgical personnel, while maintaining the sterility of the instruments. The present invention also helps to protect instruments during surgical operations from possible damaging contact with each other. The invention also guards against possible cross contamination among various surgical instruments.

The invention generally comprises a formed, free-standing body or rack provided with a plurality of grooves or slots which are separated by raised partitions. The grooves are adapted to receive a variety of differently configured surgical instruments. The surgical rack is preferably designed to hold and isolate the instruments in an inclined orientation, such that the proximate ends or handles of the instruments are readily accessible to the surgeon. The remote or patient ends of the instruments are maintained in the grooves below the level of the partitions. In such a fashion, the remote end of each instrument is substantially removed from the possibility of inadvertent contact by the surgeon or other attending medical personnel. The sharpened points or cutting surfaces of the instruments are likewise isolated from contact with each other.

The present invention also includes a disposable surgical towel or drape which is attachable to the surgical rack so as to form an integral unit. In this connection, the surgical towel or drape is secured to the bottom surface of the surgical rack so as to define a sterile field thereabout. This field accommodates the placement and/or organization of instruments or other sterile surgical items. The surgical drape also preserves the sterility of the proximate or handle ends of the surgical items.

The present invention provides a number of advantages over prior art systems and methods for preventing inadvertent laceration or puncture from surgical instruments. One such benefit is the isolation of the potentially contaminated cutting surfaces and/or sharpened edges or points of such instruments. This is achieved by situating these cutting surfaces, edges or points in recessed portions of the surgical rack such that their exposure is brought about only as a result of the intentional extraction of an instrument.

A second advantage of the present invention lies in the reduction or elimination of the need, in many instances, for an assisting nurse to organize the instruments during the surgical procedure. Due to the nature of the present invention, instrument organization may be accomplished by the physicia himself. Additionally, the integration of the drape and the surgical rack reduces or eliminates the need for a preparation nurse or assistant to use sterile gloves to place the system on a surgical tray, since this task may instead be accomplished by the use of surgical transfer forceps.

Yet other advantages include a reduction in the risk of penetrating or otherwise comprising a sterile field drape by puncture or laceration. This risk is addressed by the ability to place sharp or pointed objects directly on the surgical rack. The surgical rack also allows for more ready retrieval of instruments than would otherwise be possible off of a flat surgical drape.

The use of the present system also provides for savings in terms of both costs and time in connection with the use of hypodermic syringes. This is achieved by the present invention by reducing or eliminating the need to recap syringes during surgical procedures, or alternatively, to use additional syringes.

Other advantages of the present invention will become obvious to those skilled in the art in light of the following description and accompanying drawings.

BRIEF DESCRIPTION OF THE DRAWINGS

FIG. 2 illustrates a top view of the embodiment of the invention illustrated in FIG. 1.

DETAILED DESCRIPTION OF THE DRAWINGS

Figure 1:
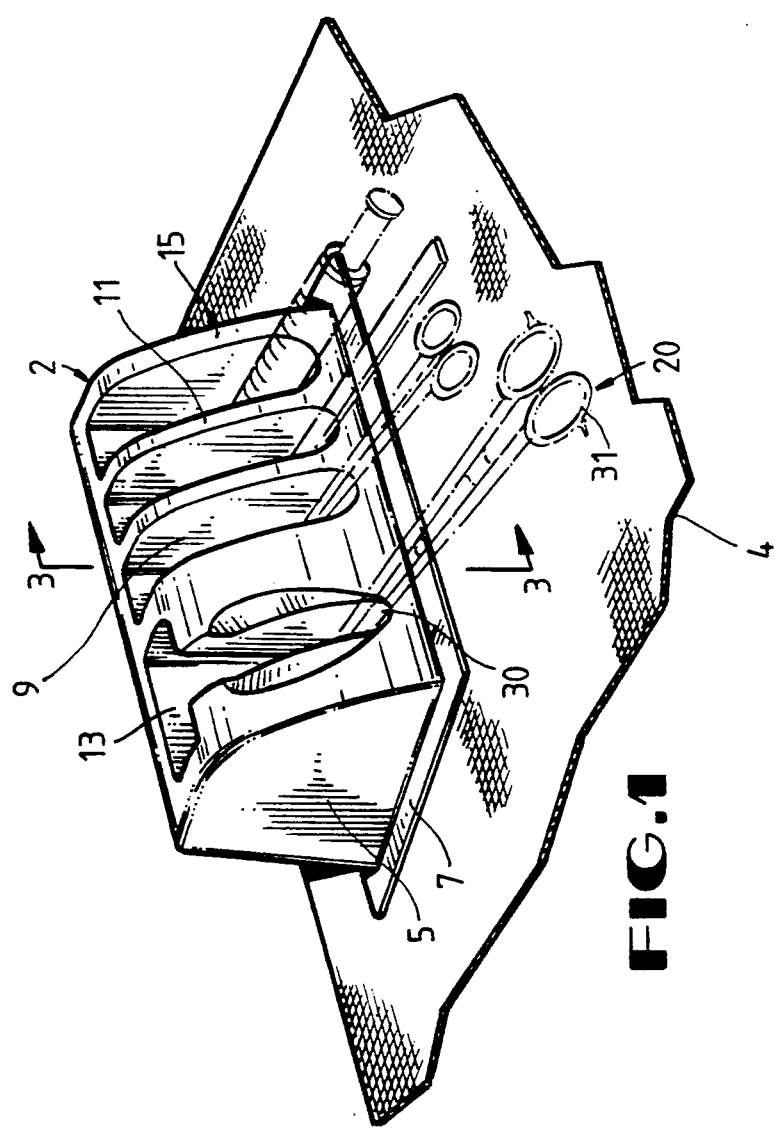
FIG. 1 illustrates a perspective view of a preferred embodiment of the invention including a surgical rack as it may be affixed to a surgical drape.

The components of the present invention may be generally seen by reference to the drawings. FIG. 1 shows a surgical rack 2 of the invention as it may be positioned relative to a surgical drape 4 so as to form an integral unit. As illustrated, surgical rack 2 is positioned in the upper right hand quadrant of the surgical drape 4 to aid in packaging and preparation of the unit preliminary to a surgical procedure, and as will be further discussed herein.

Figure 3:
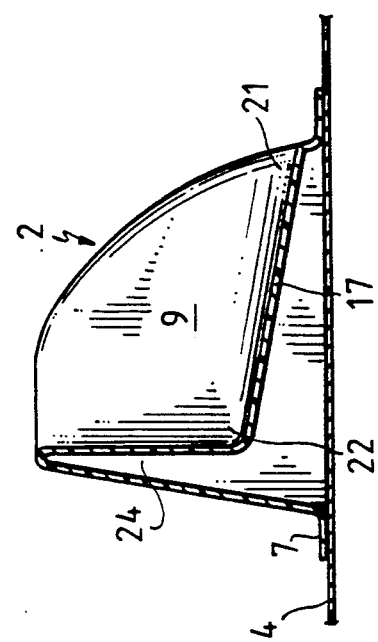
FIG. 3 illustrates a side cutaway view of the embodiment of the invention taken along the section lines 3—3 in FIG. 1.

Surgical rack 2 generally comprises a body 5 including a base or flange 7 about its bottommost extent. In a preferred embodiment, body 5 is provided with a series of specially configured grooves or channels 9 about its upper surface which are separated by a corresponding series of partitions or dividing walls 11 and sidewalls 15. As illustrated in FIG. 1, channels or grooves 9 are adapted to hold and isolate a variety of instruments 20. Grooves 9 may therefore adopt a variety of configurations depending on their intended application. Thus, body 5 may be provided with a "T-shaped" groove 13 and/or linear grooves 9 as illustrated in FIGS. 1-3. Grooves 9 may also be provided with corrugations (not shown) or other means to securely hold the surgical instruments. Preferably, dividing walls 11 taper at their uppermost extent so as to facilitate instrument removal. Accordingly, grooves 9 taper downwardly as illustrated.

Each groove 9 defines an open end and a closed end 22. (See FIG. 3). The closed end 22 of groove 9 terminates in the raised back portion 24 of body 5. The surgical rack is adapted to be used such that the open end 21 of groove 9 faces the physician so as to facilitate instrument retrieval and identification.

Referring to FIG. 3, grooves 9 preferably define a upwardly sloping bottom surface 17 when viewed in side cross section. Instruments placed in grooves 9 therefore adopt a tilted orientation such that the remote patient end 30 of said instruments is raised with respect to the proximal surgeon end or handle 31. This orientation serves two functions. First, this upwardly slanted orientation allows easier access and identification of the instruments 20 to the surgeon. Secondly, nonviscous fluids or the like remaining on the instruments will be moved outwardly down the inclined bottom surface 17 and will therefore be unable to collect or pool. To further prevent such pooling, bottom surface 17 may be provided with drainage apertures or the like (not shown).

Body 5 is preferably comprised of single sheet PVC or styrene which is thermovacuum molded in a conventional fashion. In this connection, it is envisioned that body 5 is hollow about its interior. (See FIG. 3). Back wall 24, partitions 11 and sidewalls 15 are therefore comprised of a double layer of material which offers additional safeguards against puncture or laceration to medical personnel. Such double wall construction also helps ensure against the inadvertent breach of the sterile field created by drape 4.

Body 5 is preferably provided with a base or flange 7. Flange 7 serves to stabilize body 5 so as to maintain a secure, upright orientation. Flange 7 also serves as an attachment site for surgical drape 4. In a preferred embodiment, surgical rack 2 is secured to drape 4 via a contact adhesive such as a 957 contact adhesive manufactured by The 3M Company. To aid in packaging, it is desirable to secure the surgical rack 2 to the upper right-hand quadrant of the surgical drape 4 as illustrated in FIG. 2. In this fashion, the combination surgical rack 2 and drape 4 may be readied for use merely by grasping a corner of the drape 4 from the opened end of a sterilized package containing the system and allowing the weight of the rack to unfold the drape 4. As noted, this process may be carried out by surgical transfer forceps to preserve the sterility of the system.

Surgical drape 4 preferably comprises a laminated plastic-paper composition such as the Poly-Back drape manufactured by Graham Medical Products, Inc. of Green Bay, Wis. Other surgical towels are also envisioned in the spirit of the present invention.

In an alternate embodiment, the surgical rack 2 may be used individually and apart from surgical drape 4. The use of the rack 2 in this manner may be desirable in a outpatient procedure such as dermatology, otorhinolaryngology, dentistry, etc. In such cases, the remote patient end of the surgical instrument is placed on the rack 2 during the surgical procedure and is therefore maintained in a sterile condition.

What I claim is:

1. A combination surgical rack and sterile field comprising:
   a body having a base, an upper surface, and a plurality of equipment storage grooves disposed in said upper surface and isolated from one another by partitions therebetween:
   each said groove having a closed inner end, an open outer end, and a bottom surface inclined toward said open end; and
   a sterile drape attached to the bottomside of the base of said body.

2. The surgical rack of claim 1 wherein said equipment storage grooves are provided with corrugations to aid in the placement of surgical instruments.

3. The surgical rack of claim 1 wherein said equipment storage grooves are provided with a drainage means.

4. The surgical rack of claim 1 wherein the base of said body is attached to the upper quadrant of said drape.

5. The surgical rack of claim 1 wherein the grooves are configured to nonsecurably receive the sharpened or pointed ends of surgical instruments.

6. The surgical rack of claim 1 wherein the storage grooves taper downwardly toward their open outer end.

7. The surgical rack of claim 1 wherein said storage rack is integral molded polyvinyl chloride or polystyrene.

8. A surgical rack and storage system comprising:
   a "L" shaped body defining an upright portion and a base portion;
   a series of ribs joining said upright and base portions so as to define a series of grooves therebetween, where said grooves are configured to receive the remote, patient end of a surgical instrument; and
   an adhesive coating on the base portion, adherable to a surgical drape.

9. The surgical rack of claim 8 wherein said surgical rack is secured to a surgical drape so as to provide for a sterile field about said body.

10. A surgical instrument storage system comprising:
    a body defining an upright portion and a base portion where said upright and base portions are coupled together via a series of partitions organized in a selectively spaced orientation so as to define a series of substantially linear grooves therebetween;
    each said groove including a first, closed end which merges with the upright portion of the body, an open second end, and a bottommost surface which is inclined toward said open end;
    an attachment flange extending around the bottommost periphery of the base portion; and
    a surgical drape affixed to said flange.

11. A combination surgical rack and sterile field for surgical instruments, comprising:
- a body having a base and top and front surfaces;
- at least one groove formed in the body and extending from the top of the body down the front of the body;
- each said groove having a bottom surface and walls configured to receive and isolate the patient end of a surgical instrument such that the patient end may be viewed while resting on the bottom surface with the handle end of the instrument extending outside the groove beyond the front surface of the body; and
- a surgical drape attached to the base.

12. The rack and sterile field of claim 11 wherein the bottom surface of the groove is inclined to face toward the front of the body.

13. A combination surgical rack and sterile field for surgical instruments, comprising:
- a body having a base and top and front surfaces;
- a plurality of laterally isolated grooves formed in the top and front surfaces of the body, each groove extending from the top of the body down the front of the body and including a bottom surface;
- each said groove and its bottom surface configured to receive the patient or working end of a surgical instrument with the handle of the instrument extending outside the groove beyond the front surface of the body;
- a surgical drape attached to the base of the body in a manner to enable the body to stand on the surgical drape.

14. The rack and sterile field of claim 13 which further comprises at least one additional groove disposed in laterally isolated relation with each other said groove.

15. The rack and sterile field of claim 13 wherein the body further comprises back and side surfaces which are spaced from the walls of the grooves.

16. An apparatus for temporarily storing sharp surgical instruments used during surgery, comprising:
- a disposable body having a base, a top surface, a bottom surface, a first end, a second end, and a plurality of grooves extending along the top surface between the first end and the second end; the grooves being isolated from one another by partitions therebetween; each groove configured to receive and nonsecurably support the sharp end of a surgical instrument; the inner surfaces of the grooves and partitions formed of a flexible, resilient material.

17. The apparatus of claim 16 wherein at least a portion of the bottom surface of the body has an adhesive coating adherable to a surgical drape.

18. The apparatus of claim 16 wherein the inner surfaces of the grooves and partitions are puncturable by surgical needles for storage of the needles during surgery.

19. The apparatus of claim 16 wherein the grooves include at least one T-shaped groove.

20. The apparatus of claim 16 wherein each groove is open at the first end of the body and is closed at the second end of the body.

21. The apparatus of claim 16 wherein each groove is inclined between the first end and the second end of the body.

22. The apparatus of claim 16 wherein the body is formed of flexible plastic.

* * * * *